US009932285B2

(12) United States Patent
Allan et al.

(10) Patent No.: US 9,932,285 B2
(45) Date of Patent: Apr. 3, 2018

(54) PHENOLIC RESIN PRECURSORS VIA SUPERCRITICAL WATER

(71) Applicants: Graham Allan, Kenmore, WA (US); Thomas E. Loop, Seattle, WA (US); James D. Flynn, Auburn, WA (US)

(72) Inventors: Graham Allan, Kenmore, WA (US); Thomas E. Loop, Seattle, WA (US); James D. Flynn, Auburn, WA (US)

(73) Assignee: Xtrudx Technologies, Inc., Seattle, WA (US)

( * ) Notice: Subject to any disclaimer, the term of this patent is extended or adjusted under 35 U.S.C. 154(b) by 426 days.

(21) Appl. No.: 14/549,508

(22) Filed: Nov. 20, 2014

(65) Prior Publication Data

US 2015/0148566 A1 May 28, 2015

Related U.S. Application Data

(63) Continuation-in-part of application No. 13/297,217, filed on Nov. 15, 2011, now Pat. No. 8,980,143, (Continued)

(51) Int. Cl.
*B29B 17/02* (2006.01)
*B29C 47/10* (2006.01)
(Continued)

(52) U.S. Cl.
CPC ............ *C07C 37/004* (2013.01); *B01J 3/008* (2013.01); *B01J 8/0045* (2013.01); *B01J 8/1836* (2013.01);
(Continued)

(58) Field of Classification Search
CPC . B29B 17/02; B29B 2017/0293; B29B 17/00; B29B 2017/00; B29B 2017/001;
(Continued)

(56) References Cited

U.S. PATENT DOCUMENTS 3,293,200 A * 12/1966 MacGregor ............ C09J 161/06
428/529
4,233,465 A * 11/1980 Gallivan .................. C08G 8/28
568/727
(Continued)

*Primary Examiner* — Joseph Drodge
(74) *Attorney, Agent, or Firm* — Thomas E. Loop

(57) ABSTRACT

A method for transforming selected plant or plant-derived materials, and optionally selected waste plastics, into a plurality of phenolic reaction products having a lower sulphur content than the original feedstock, via supercritical water is disclosed. The method comprises: conveying the selected plant or plant-derived materials, and optionally waste plastic material, through an extruder, wherein the extruder is configured to continuously convey the selected feedstock to a supercritical fluid reaction zone; injecting hot compressed water into the supercritical fluid reaction zone, while the extruder is conveying the selected plant and/or plant-derived mixture and optionally waste plastic material into the supercritical fluid reaction zone so as to yield a water-containing mixture; retaining the mixture within the reaction zone for a period of time sufficient to yield the plurality of phenolic reaction products having a lower sulphur content than the original feedstock. The reaction zone may be characterized by a tubular reactor having an adjustably positionable inner tubular spear, wherein the tubular reactor and the inner tubular spear further define an annular space within the reaction zone, and wherein the mixture flows through the annular space and into a reaction products chamber for separation into three phases.

8 Claims, 2 Drawing Sheets

Related U.S. Application Data which is a continuation-in-part of application No. 12/828,102, filed on Jun. 30, 2010, now Pat. No. 8,057,666, which is a continuation-in-part of application No. 12/402,489, filed on Mar. 11, 2009, now Pat. No. 7,955,508.

(60) Provisional application No. 61/906,756, filed on Nov. 20, 2013.

(51) Int. Cl.

| | | |
|---|---|---|
| *B29C 47/88* | (2006.01) | |
| *C07C 37/70* | (2006.01) | |
| *C07C 37/86* | (2006.01) | |
| *C08J 11/14* | (2006.01) | |
| *B01J 19/18* | (2006.01) | |
| *B01J 8/20* | (2006.01) | |
| *B01J 8/42* | (2006.01) | |
| *C07C 37/00* | (2006.01) | |
| *B01J 8/18* | (2006.01) | |
| *B01J 19/08* | (2006.01) | |
| *B01J 3/00* | (2006.01) | |
| *B01J 8/00* | (2006.01) | |

(52) U.S. Cl.
CPC . *B01J 8/20* (2013.01); *B01J 8/42* (2013.01); *B01J 19/087* (2013.01); *B29B 17/02* (2013.01); *B29C 47/10* (2013.01); *B29C 47/88* (2013.01); *C07C 37/005* (2013.01); *C07C 37/70* (2013.01); *C08J 11/14* (2013.01); *B01J 2219/089* (2013.01); *B01J 2219/0854* (2013.01); *B01J 2219/182* (2013.01); *Y02P 20/544* (2015.11)

(58) Field of Classification Search
CPC ..... B29C 47/00; B29C 47/10; B29C 47/1009; B29C 47/1018; B29C 47/109; B29C 47/40; B29C 47/88; B29C 47/8805; C07C 37/00; C07C 37/005; C07C 37/68; C07C 37/685; C07C 37/70; C07C 37/72; C07C 37/86; C07C 37/004; C07C 37/006; C08J 11/00; C08J 11/14; C08J 11/16; C08J 11/10; B01J 8/20; B01J 8/42; B01J 19/087; B01J 3/008; B01J 8/1836; B01J 8/0045; B01J 2219/089; B01J 2219/182; B01J 2219/0854; B01J 8/008; B01J 16/00; B01J 2219/24; B01J 19/1812; B01J 19/1843; B01J 19/18; B01J 8/00; B01J 2017/0203; Y02P 20/544; Y02P 2219/089; B01D 17/00; B01D 17/005

USPC ........ 210/175, 177, 180–182, 259, 511, 634, 210/639, 758–761, 774, 749, 808; 264/37.1, 37.18, 211.21, 211.23, 211.24, 264/11–13, 454; 241/20, 24, 28; 44/307, 44/308, 605, 606; 422/138, 198, 199, 422/208, 602, 606, 608, 618, 242; 219/600, 618, 628, 630, 635; 71/11–13; 554/8–23, 174, 175; 528/480, 483, 502, 528/502 R, 502 A, 502 F, 503

See application file for complete search history.

(56) References Cited

U.S. PATENT DOCUMENTS

| | | | | |
|---|---|---|---|---|
| 4,942,269 | A * | 7/1990 | Chum | C07C 37/005 208/96 |
| 5,223,601 | A * | 6/1993 | Chum | C07C 37/52 428/514 |
| 5,386,055 | A * | 1/1995 | Lee | B01J 3/008 210/180 |
| 5,807,952 | A * | 9/1998 | Agblevor | C07B 41/02 527/400 |
| 6,676,716 | B2 * | 1/2004 | Fujimura | C10J 3/523 422/140 |
| 7,235,219 | B2 * | 6/2007 | Nakajima | C08J 3/09 264/211.21 |
| 7,399,408 | B2 * | 7/2008 | Joussot-Dubien | A62D 3/20 210/179 |
| 7,799,835 | B2 * | 9/2010 | Smith | B29B 17/02 209/552 |
| 7,923,039 | B2 * | 4/2011 | Cornish | B01D 11/0284 209/12.1 |
| 7,955,508 | B2 * | 6/2011 | Allan | B01J 3/008 210/749 |
| 8,057,666 | B2 * | 11/2011 | Allan | B01J 3/008 210/175 |
| 8,342,735 | B2 * | 1/2013 | Black | C12M 35/04 366/78 |
| 8,980,143 | B2 * | 3/2015 | Loop | B01J 3/008 210/175 |
| 2003/0021915 | A1 * | 1/2003 | Rohatgi | B27N 3/007 428/15 |
| 2003/0042645 | A1 * | 3/2003 | Ichikawa | B29C 47/0007 264/102 |
| 2005/0242464 | A1 * | 11/2005 | Goto | B29B 17/02 264/211.24 |
| 2007/0161095 | A1 * | 7/2007 | Gurin | C12P 7/10 435/134 |
| 2008/0113146 | A1 * | 5/2008 | Wright | B29B 17/02 428/95 |
| 2010/0210745 | A1 * | 8/2010 | McDaniel | C09D 5/008 521/55 |

* cited by examiner

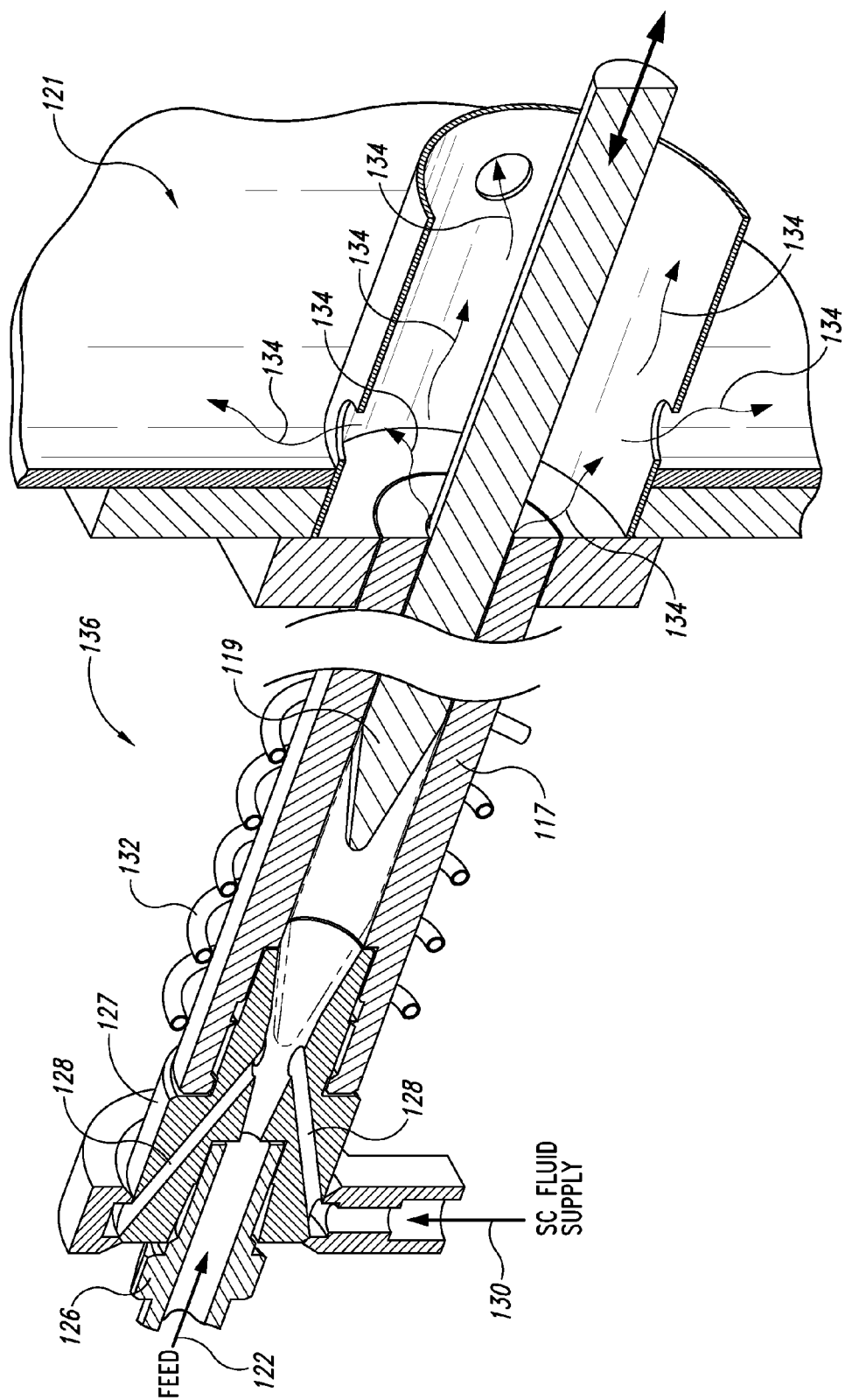

PHENOLIC RESIN PRECURSORS VIA SUPERCRITICAL WATER

CROSS-REFERENCE TO RELATED APPLICATIONS

This application is a continuation-in-part of U.S. application Ser. No. 13/297,217 filed on Nov. 15, 2011 (allowed), which application claims the benefit of priority to U.S. patent application Ser. No. 12/828,102 filed on Jun. 30, 2010 (now U.S. Pat. No. 8,057,666) and U.S. application Ser. No. 12/402,489 filed on Mar. 11, 2009 (now U.S. Pat. No. 7,955,508), which applications claims the benefit of priority to U.S. Provisional Application No. 61/035,380 filed on Mar. 11, 2008 and U.S. Provisional Application No. 61/110,505 filed on Oct. 31, 2008, which applications are all incorporated herein by reference in their entireties for all purposes. This application also claims the benefit of priority to U.S. Provisional Application No. 61/906,756 filed on Nov. 20, 2013.

TECHNICAL FIELD

The present invention relates generally to the conversion of plant or plant-derived polyphenolic materials into simpler phenols suitable for use as components for wood adhesives and, more specifically, to machines and methods of transforming the family of naturally-occurring lignins into smaller molecules by reaction with a hot compressed and/or supercritical water.

BACKGROUND OF THE INVENTION

The Sun pours down onto the Earth a vast quantity of radiant energy. Some of this energy, together with carbon dioxide and water, Nature traps as vegetation. A substantial part of the vegetation is a giant aromatic molecule that functions as a natural adhesive holding other parts of the plant together. This functioning has been copied by humans in the development of adhesives to glue together small pieces of wood to manufacture larger useful composite products exemplified by plywood, oriented strand board, particleboard and the like. The recognition of the chemical similarity between the synthetic and natural adhesives has repeatedly prompted the idea of using the natural adhesive in the man-made composite wood products in place of the synthetic. In spite of very extensive research efforts success has not been achieved for several distinct reasons. The first of these was economics. For many years the extremely low price of the main component of the synthetic adhesives, that was derived from petroleum, made its replacement by the natural adhesive marginal. With the rise in the value of petroleum this is no longer the case because the price of the derived main synthetic adhesive component has risen about fifteenfold. Of course, the natural aromatic adhesive has to be isolated from the vegetation and there are associated costs. In addition, the isolation procedures are usually part of reactions carried out on the vegetation for other reasons. The most common of these is the pulping of wood to yield fibers for papermaking. The aromatic natural adhesive polymer that is mostly available in abundance is designated kraft lignin and is part of the aqueous so-called "black liquor" as a polysodium salt. This liquor is usually concentrated and is burned in admixture with fuel oil to recover the inorganic chemicals therein. The fuel value of the liquor is very low. To isolate the kraft lignin from the black liquor requires acidification to precipitate the sodium-free form followed by filtration and drying of the gelatinous product. This is difficult to do and the isolated kraft lignin is therefore not inexpensive. Besides the cost factor of the processing, the isolated kraft lignin cannot be used as a wood adhesive component for two main technical reasons. The first is the wide range of molecular sizes present and the second, the relatively low level of reactive functionality with methyleneglycol, the other main component of the synthetic wood adhesive. The larger molecules in the kraft lignin molecular mixture cannot penetrate into the wood infrastructure so as to bond and reinforce the weakened surface layers damaged by the cutting or sawing processes that generated the small wood pieces.

The problem facing composite scientists has therefore been how to overcome these drawbacks to utilize polyphenolic materials from plants or plant-derived feedstocks in a large-scale, commercially practical, and energy efficient way such that the petroleum-derived components of wood adhesives can be at least partly replaced.

One of the most intriguing and environmentally sound approaches to breaking down molecules is simply to use water alone, heated to its supercritical state. About a decade ago this chemical-free technology was comprehensively discussed in an English language review by P. E. Savage (Chem. Rev. 1999, 99, 609). Since then few modern reviews have appeared. However, numerous articles, mostly from Japan and China, have appeared each year dealing with the reactive power of supercritical water. All of these publications emphasize that when water is heated to 374.4 C or above, the pressure concomitantly generated is 217.7 atm and above. The water then becomes a powerful new reactive solvent. Temperatures above 400 C seem to make the water even more effective in its new role. For example, it now dissolves nonpolar substances such as plant polyphenolics.

These and numerous other similar reactions (J. A. Onwudili & P. T. Williams, Chemosphere 2009, 74(6), 787) demonstrate clearly that chemical bonds can be broken down by treatment with supercritical water only, without the use of any catalysts. When a covalent single bond between two carbons atoms is cleaved, two free radicals are created, one on each carbon atom formerly at the ends of the single bond. These types of linkages join the aromatic rings making up much of the plant phenolic adhesive. The high reactivity of these free radical entities is probably involved in the formation of undesirable crosslinked and other undesirable large macromolecular complexes useless as adhesive precursors. These pathways are apparently blocked during the reactions of supercritical water which yields hydrogen atoms that combine with the free radical sites to deactivate them. This has actually been demonstrated by the use of deuterium oxide in place of water (hydrogen oxide) and the consequent finding of deuterium in the fragments. It has also been shown that sulfur-containing molecules can be desulfurized by cleavage of the carbon-sulfur bonds with expulsion of the sulphur atoms as hydrogen sulfide. Some of the established procedures for the isolation of the plant phenolic material introduce sulfur atoms into the isolated material. However, since nearly all water-substrate reactions have been run in a batch mode on a very small scale, the chemistry so elegantly elucidated there does not provide answers to the questions necessary for the future development of a commercially-sized, practical, continuous, supercritical water-based process.

The present invention fulfills these needs and provides for further related advantages.

SUMMARY OF THE INVENTION

The present invention in one embodiment is directed to a new method for transforming a selected polyphenolic plant or plant-derived material into a plurality of essentially monomolecular reaction products suitable for use as precursors for wood adhesive formulations and having a sulphur content of less than 10% by weight. The innovative method of the present invention comprises at least the following steps: conveying the selected plant or plant-derived material (e.g., scrap wood, branches, bark, agricultural residues, grasses, pulping liquors or a combination thereof) through an extruder (single or twin screw) so as to define a selected plant or plant-derived material flowstream, wherein the extruder is configured to continuously convey the selected feedstock material from an upstream inlet to a supercritical fluid reaction zone; injecting hot compressed water into the supercritical fluid reaction zone while the extruder is conveying the selected plant-derived material flowstream into the supercritical fluid reaction zone so as to yield a mixture; retaining the mixture within the reaction zone for a period of time (e.g., from about 0.4 to about 100 seconds) sufficient to yield the plurality of reaction products, wherein the reaction zone is defined by a tubular reactor shell having an inner tubular spear, wherein the tubular reactor and the inner tubular spear further define an annular space within the reaction zone, and wherein the mixture flows through the annular space (and wherein the inner tubular spear is adjustably movable in back and forth directions within the tubular reactor so as to selectably increase or decrease the volume of the reaction zone); and expelling the plurality of reaction products out of the supercritical fluid reaction zone and into a reaction products chamber. The method may further comprise a step of easily separating the plurality of reaction products into an aqueous phase, a non-aqueous phase and a gaseous phase.

In another embodiment, the present invention is directed to an innovative tube and spear reactor as herein shown and described, as well as to related extruder-based machinery and fluid expansion chambers.

These and other aspects of the present invention will become more evident upon reference to the following detailed description and accompanying drawings. It is to be understood, however, that various changes, alterations, and substitutions may be made to the specific embodiments disclosed herein without departing from their essential spirit and scope.

DETAILED DESCRIPTION OF INVENTION

The present invention in one embodiment is directed to a supercritical fluid conversion machine/system capable of converting a selected plant or plant-derived material into a plurality of reaction products. In the context of the present invention, the term "plant or plant-derived" means any naturally originating, carbon-based organic matter, containing a multiplicity of single carbon-carbon bonds together with a multiplicity of aromatic ring structures.

As shown, the plant conversion machine/system of the present invention comprises, in fluidic series, three discreet zones: namely, (1) an extruder-based conveying zone; (2) a supercritical fluid reaction zone; and (3) a reaction products separation zone.

In accordance with the novel approach of the present invention, a specialized extruder conveys the selected plant or plant-derived materials from an upstream hopper to the downstream supercritical fluid reaction zone, while increasing the pressure from about atmospheric to greater than about 3,200 psi. The extruder-based approach is important because it enables the conveyance of near-solid materials (as opposed to conventional slurry pumping technologies used in the prior art). The heated and pressurized plant or plant-derived materials exit the extruder through a specialized die connected to a manifold that includes a plurality of circumferentially positioned supercritical fluid injection channels configured to inject hot compressed water (or other fluid) into the supercritical fluid reaction zone.

In a preferred embodiment, hot compressed water is injected into the supercritical fluid reaction zone by way of the injection channels while the extruder is conveying the selected polymeric materials into the supercritical fluid reaction zone so as to yield a mixture (not shown). The supercritical fluid reaction zone further heats the flowing and pressurized plant or plant-derived materials and hot compressed water mixture to conditions at or above supercritical by means of a circumferentially positioned, high efficiency alternating current induction coil (which, in turn, is connected to an induction heater) to thereby yield the plurality of reaction products. The resulting liquefied and/or gaseous reaction products are then conveyed through a highly innovative spear-and-tube reactor.

The spear-and-tube reactor of the present invention allows a controlled and/or minimal amount of supercritical water to enter into the system (i.e., preferably less than about 100% to about 20% by weight basis). More specifically, the reaction zone is defined by a tubular reactor shell having an inner tubular spear, wherein the tubular reactor shell and the inner tubular spear further define an annular space within the reaction zone. As shown, the mixture of plant or plant-derived materials and hot compressed water yield the plurality of reactions products that flow through the annular space and are expelled into an innovative expansion/separation chamber. The expansion/separation chamber preferably contains liquid water and a hydrocarbon solvent to facilitate liquid-liquid extraction and phase separation of the resulting mixture of water-soluble and water-insoluble substances. As further shown, the inner tubular spear is adjustably movable in back and forth directions within the tubular reactor shell by means of a servo cylinder so as to selectable increase or decrease the volume of the reaction zone.

Without necessarily prescribing to any particular scientific theory, it is believed that at supercritical conditions the water component is at a supercritical state, thereby enabling (in the context of selected plant or plant-derived material) the rapid cleavage of some of the single carbon to carbon linkages therein with the simultaneous capture of hydrogen atoms and hydroxyl moieties from the water. As a consequence, a whole range of smaller molecules of various lengths are formed that are capable of functioning as components of wood adhesive formulations.

The present invention is also directed to a method for converting plant or plant-derived materials into a plurality of reaction products having a lower sulphur content than the original feedstck. Accordingly, and in another embodiment, a method of the present invention comprises the steps of: providing an elongated conveying zone that contains two or more elongated rotatable shafts having a plurality of flighted screws positioned lengthwise within an elongated conveying section housing, wherein the plurality of flighted screws are positioned about each respective two or more elongated rotatable shafts, and wherein the two or more elongated rotatable shafts are configured to continuously convey the selected plant or plant-derived materials (optionally together with water or other fluid/liquid) from an upstream inlet to a supercritical fluid reaction zone while increasing the pressure of the selected plant or plant-derived materials from about atmospheric at the inlet to greater than about 22.1 MPa at the supercritical fluid reaction zone; conveying the selected materials through the elongated conveying zone and into the supercritical fluid reaction zone; heating and further pressurizing the mixture within the supercritical fluid reaction zone, while injecting hot compressed and/or supercritical water into the supercritical fluid reaction zone, to yield a plurality of reaction products, wherein heat energy is supplied by means of an induction heating coil positioned circumferentially about the supercritical fluid reaction zone; retaining the mixture within the supercritical fluid reaction zone for a period of time sufficient to yield the plurality of reaction products; expelling the plurality of reaction products out of the supercritical fluid reaction zone and into a separation zone; and separating the plurality of reaction products into at least a water-soluble fraction and an organic solvent soluble fraction.

In this method, the period of time that the mixture of plant-derived material and water is retained within the supercritical fluid reaction zone generally ranges from about 0.4 to about 100 seconds (but may include much greater periods of time up to a few minutes in duration). This method may also comprises the further steps of adding a plurality of electrically conductive particles to the mixture of selected plants and plant-derived materials and water such the plurality of electrically conductive particles are heated while passing through the induction coil.

Waste plastics exemplified by polyethylene, polypropylene and polystyrene from plastic containers and film and the like can also be included with the plant or plant-derived materials so that their water-insoluble breakdown products from the continuous reaction with supercritical water will dissolve in the converted, water-insoluble products from the plant or plant-derived material and hence reduce the viscosity thereof and facilitate the separation from the aqueous phase that will contain water-soluble sugars and the like.

Finally, and for purposes of efficient heat transfer across the flowing stream of plant or plant-derived material, with or without the addition of waste plastic, it is contemplated that a suitable heat transfer agent such as, for example, a recyclable low melting metal (tin, mp 232° C. or lead, mp 327° C.) or metal alloy, preferably Wood's metal (an alloy of Bismuth 50%, Cadmium 12.5%, Lead 25% and Tin 12.5%, mp 73-77° C.) may be added to the plant or plant-derived feedstock prior to its introduction into the co-rotating twin screw extruder.

While the present invention has been described in the context of the embodiments described herein, the invention may be embodied in other specific ways or in other specific forms without departing from its spirit or essential characteristics. Therefore, the described embodiments are to be considered in all respects as illustrative and not restrictive.

In another embodiment, the present invention is directed to an innovative tube and spear reactor as herein shown and described, as well as to related extruder-based machinery and fluid expansion chambers.

These and other aspects of the present invention will become more evident upon reference to the following detailed description and accompanying drawings. It is to be understood, however, that various changes, alterations, and substitutions may be made to the specific embodiments disclosed herein without departing from their essential spirit and scope.

BRIEF DESCRIPTION OF THE DRAWINGS

The drawings are intended to be illustrative and symbolic representations of certain exemplary embodiments of the present invention and as such they are not necessarily drawn to scale. In addition, it is to be expressly understood that the relative dimensions and distances depicted in the drawings are exemplary and may be varied in numerous ways. Finally, like reference numerals have been used to designate like features throughout the views of the drawings.

FIG. 2 shows a partial cross-sectional view of a supercritical fluid reaction zone defined by a spear-and-tube reactor in accordance with an embodiment of the present invention.

DETAILED DESCRIPTION OF INVENTION

Figure 1:
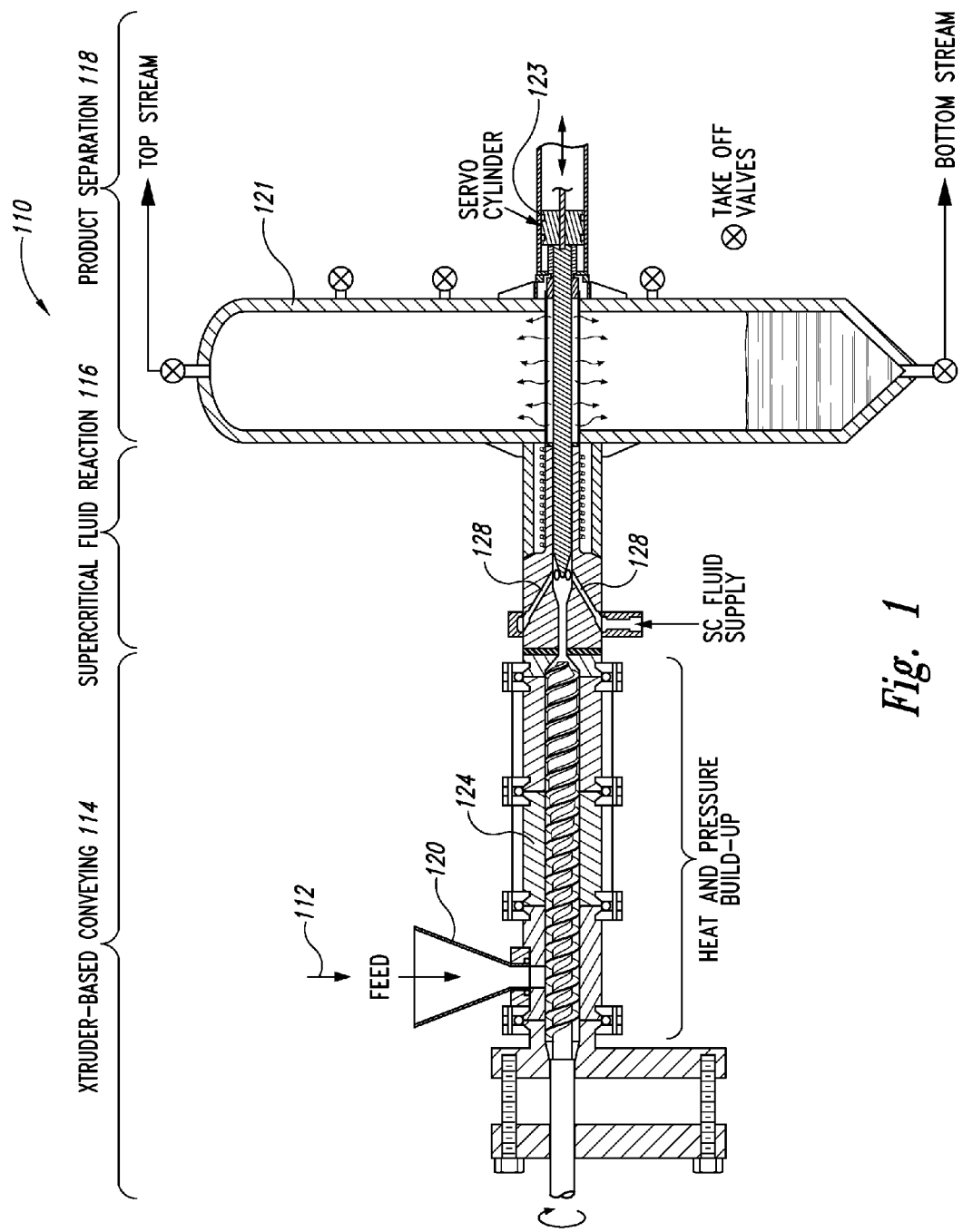
FIG. 1 shows a side elevational cross-sectional view of an extruder-fed induction-heated supercritical fluid polymer depolymerization machine in accordance with an embodiment of the present invention.

Referring now to the drawings where like numerals have been used to designate like features throughout the views, and more specifically to FIGS. 1 and 2, the present invention in one embodiment is directed to a supercritical fluid polymer depolymerization conversion machine/system 110 capable of converting a selected biomass and/or waste plastic material 112 into a plurality of reaction products (not shown). In the context of the present invention, the term "biomass" means any plant derived organic matter, including dedicated energy crops and trees, agricultural food and feed crops, agricultural crop wastes and residues, wood wastes and residues, aquatic plants, algae, animal wastes, municipal wastes, and other like organic materials—whereas the term "waste plastic" means a synthetic polymer. As shown, the polymer conversion machine/system 110 of the present invention comprises, in fluidic series, three discreet zones: namely, (1) an extruder-based conveying zone 114; (2) a supercritical fluid reaction zone 116; and (3) a reaction products separation zone 118.

In accordance with the novel approach of the present invention, a specialized extruder conveys the selected biomass and/or waste plastic materials 112 from an upstream hopper 120 to the downstream supercritical fluid reaction zone 116, while increasing the pressure from about atmospheric to greater than about 3,200 psi. The extruder-based approach is important because it enables the conveyance of near-solid materials (as opposed to conventional slurry pumping technologies used in the prior art). The heated and pressurized near-sold materials (biomass and/or waste plastic) 122 exits the extruder 124 through a specialized die 126 connected to a manifold 127 that includes a plurality of circumferentially positioned supercritical fluid injection channels 128 configured to inject hot compressed water 130 (or other fluid) into the supercritical fluid reaction zone 116.

In a preferred embodiment, hot compressed water 130 is injected into the supercritical fluid reaction zone 116 by way of the injection channels 128 while the extruder 124 is conveying the selected polymeric materials 112 into the supercritical fluid reaction zone 116 so as to yield a mixture (not shown). The supercritical fluid reaction zone 116 further heats the flowing and pressurized polymeric materials 122 and hot compressed water 130 mixture to conditions at or above supercritical by means of a circumferentially positioned, high efficiency alternating current induction coil 132 (which, in turn, is connected to an induction heater (not shown)) to thereby yield the plurality of reaction products 134. The resulting liquefied and/or gaseous reaction products 134 are then conveyed through a highly innovative spear-and-tube reactor 136.

As best shown in FIG. 2, the spear-and-tube reactor 136 of the present invention allows a controlled and/or minimal amount of supercritical water to enter into the system (i.e., preferably less than about 100% to about 20% by weight basis). More specifically, the reaction zone 116 is defined by a tubular reactor shell 117 having an inner tubular spear 119, wherein the tubular reactor shell 117 and the inner tubular spear 119 further define an annular space within the reaction zone. As shown, the polymeric materials 122 and hot compressed water 130 mixture yield the plurality of reactions products 134 that flow through the annular space and are expelled into an innovative expansion/separation chamber 121. The expansion/separation chamber 121 preferably contains liquid water and a hydrocarbon solvent to facilitate liquid-liquid extraction and phase separation of the resulting neodiesel and water. As further shown, the inner tubular spear 119 is adjustably movable in back and forth directions within the tubular reactor shell 117 by means of a servo cylinder 123 so as to selectable increase or decrease the volume of the reaction zone.

Without necessarily prescribing to any particular scientific theory, it is believed that at supercritical conditions the water component is at a supercritical state, thereby enabling (in the context of a selected biomass material) the rapid hydrolysis and depolymerization of the surrounding biomass's main polysaccharide components (cellulose and hemicellulose) into one or more fermentable sugars, and the main polyphenolic components into one or more simple aromatic compounds. In the context of one or more waste plastics, supercritical water (SCW) breaks down, for example, polyethylene (PE) by cleaving the carbons at various locations along the backbone and simultaneously capturing hydrogen atoms from the water. As a consequence a whole range of linear hydrocarbons of various lengths are formed. Most of these have been found to be soluble in regular gasoline and may be most readily utilized in the automobile fuel market. In the case of polypropylene (PP) the breakdown fragments will not be linear, but branched, because of the side chain methyl groups on every other carbon atom in the polymer backbone. These branched structures have been found to be even more soluble in gasoline than their counterparts from polyethylene. Again, the specific fuel market will likely be for trucks and automobiles at some percentage addition value. When the starting renewable plastic is polystyrene (PS), the breakdown fragments are somewhat different because supercritical water does not readily cleave aromatic rings. The aliphatic backbone chain of polystyrene is of course cut by the supercritical water as with polyethylene and polypropylene backbones, but the polystyrene-derived fragments contain aromatic rings that originate from the phenyl rings. Thus, the supercritical water product has been found to be more like the aromatic components of kerosene with its alkylbenzenes currently usable in diesel. These aromatic higher boiling substances have been found to be more compatible with diesel fuel usage rather than gasoline.

The present invention is also directed to a method for converting a selected biomass and/or waste plastic material into a plurality of reaction products. Accordingly, and in another embodiment, a method of the present invention comprises the steps of: providing an elongated conveying zone that contains two or more elongated rotatable shafts having a plurality of flighted screws positioned lengthwise within an elongated conveying section housing, wherein the plurality of flighted screws are positioned about each respective two or more elongated rotatable shafts, and wherein the two or more elongated rotatable shafts are configured to continuously convey the selected biomass and/or waste plastic material (optionally together with water or other liquid) from an upstream inlet to a supercritical fluid reaction zone while increasing the pressure of the selected biomass and/or waste plastic material from about atmospheric at the inlet to about than about 22.1 MPa at the supercritical fluid reaction zone; conveying a mixture of the selected biomass and/or waste plastic material through the elongated conveying zone and into the supercritical fluid reaction zone; heating and further pressurizing the mixture within the supercritical fluid reaction zone, while injecting hot compressed and/or supercritical water into the supercritical fluid reaction zone, to yield a plurality of reaction products, wherein heat energy is supplied by means of an induction heating coil positioned circumferentially about the supercritical fluid reaction zone; retaining the mixture within the supercritical fluid reaction zone for a period of time sufficient to yield the plurality of reaction products; expelling the plurality of reaction products out of the supercritical fluid reaction zone and into a separation zone; and separating the plurality of reaction products into at least a water soluble fraction and an organic solvent soluble fraction.

In this method, the period of time that the mixture is retained within the supercritical fluid reaction zone generally ranges from about 0.4 to about 10 seconds (but may include much greater periods of time up to an hour and above). This method may also comprises the further steps of adding a phenolic compound to the plurality of reaction products to thereby retard the formation of certain degradation reaction products, as well as a step of adding a plurality of electrically conductive particles to the mixture of the selected biomass and/or waste material and water such the plurality of electrically conductive particles are heated while passing through the induction coil.

Finally, and for purposes of efficient heat transfer across the flowing biomass and/or waste plastic material fluid stream, it is contemplated that a suitable heat transfer agent such as, for example, a heavy petroleum oil or oil shale, or a recyclable low melting metal (tin, mp 232° C. or lead, mp 327° C.) or metal alloy, preferably Wood's metal (an alloy of Bismuth 50%, Cadmium 12.5%, Lead 25% and Tin 12.5%, mp 73-77° C.) may be added to biomass and/or waste plastic material feedstock prior to its introduction into the co-rotating twin screw extruder.

While the present invention has been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

What is claimed is:

1. A method for transforming selected plant or plant-derived feedstock, with or without the presence of waste plastic, into a plurality of reaction products including wood adhesive formulations, including essential water-insoluble phenolic substances capable of functioning as components of wood adhesives, the method comprising the steps of:

conveying the selected plant or plant-derived feedstock, and optionally waste plastic, through an extruder so as to define a selected material flowstream, wherein the extruder is configured to continuously convey the selected plant material alone or admixed with waste plastics, from an upstream inlet to a supercritical fluid reaction zone;

injecting hot compressed water into the supercritical fluid reaction zone while the extruder is conveying the selected plant or plant-derived/plastic mixture flowstream into the supercritical fluid reaction zone so as to contact the feedstock or admixture with supercritical water to yield a mixture;

retaining the feedstock or admixture within the reaction zone for a period of time sufficient to yield the plurality of phenolic reaction products including the wood adhesive formulations, said products having a lower sulphur content than the original selected feedstock, wherein the reaction zone is defined by a tubular reactor having an inner tubular spear, wherein the tubular reactor and the inner tubular spear further define an annular space within the reaction zone, and wherein the mixture flows through the annular space; and expelling the plurality of reaction products out of the supercritical fluid reaction zone and into a reaction products chamber for subsequent separation.

2. The method of claim 1 wherein the selected plant or plant-derived materials comprise natural or synthetic substances or a blend thereof.

3. The method of claim 2 wherein the extruder is a twin screw extruder.

4. The method of claim 2 wherein the hot compressed water is supercritical water.

5. The method of claim 4 wherein the hot compressed water is in an amount that is less than the conveyed amount of the selected plant or plant-derived feedstock or admixture on a weight percent basis.

6. The method of claim 2 wherein the period of time ranges from about 0.4 to about 100 seconds.

7. The method of claim 2 wherein the inner tubular spear is adjustably movable in back-and-forth directions within the tubular reactor so as to selectably increase or decrease the volume of the reaction zone.

8. The method of claim 7, further comprising the step of separating the plurality of reaction products into an aqueous phase, a non-aqueous phase and a gaseous phase containing hydrogen sulfide.

* * * * *